United States Patent
Weinstock

(10) Patent No.: US 11,439,331 B2
(45) Date of Patent: Sep. 13, 2022

(54) DEVICE FOR MAKING AVAILABLE ABSORBENT SAMPLE CARRIERS HAVING A QUANTITY OF DRIED LIQUID, IN PARTICULAR BLOOD

(71) Applicant: Sarstedt AG & Co. KG, Nümbrecht (DE)

(72) Inventor: Mark Weinstock, Helmenzen (DE)

(73) Assignee: Sarstedt AG & Co. KG, Nümbrecht (DE)

( * ) Notice: Subject to any disclaimer, the term of this patent is extended or adjusted under 35 U.S.C. 154(b) by 997 days.

(21) Appl. No.: 16/095,415

(22) PCT Filed: Jun. 29, 2017

(86) PCT No.: PCT/EP2017/066177
§ 371 (c)(1),
(2) Date: Oct. 22, 2018

(87) PCT Pub. No.: WO2018/002249
PCT Pub. Date: Jan. 4, 2018

(65) Prior Publication Data
US 2020/0352498 A1    Nov. 12, 2020

(30) Foreign Application Priority Data
Jun. 30, 2016  (DE) .......................... 102016211911.7

(51) Int. Cl.
*A61B 5/15* (2006.01)
*B01L 3/00* (2006.01)

(52) U.S. Cl.
CPC .... *A61B 5/150259* (2013.01); *A61B 5/15003* (2013.01); *A61B 5/150351* (2013.01);
(Continued)

(58) Field of Classification Search
CPC ........ A61B 5/150022; A61B 5/150343; A61B 5/150236; G01N 33/491; G01N 1/02
See application file for complete search history.

(56) References Cited

U.S. PATENT DOCUMENTS 4,174,048 A * 11/1979 Volpe, Jr. ........... B65D 83/0409
                                                        206/537
5,065,768 A    11/1991  Coleman et al.
(Continued)

FOREIGN PATENT DOCUMENTS

CN         1942138 A      4/2007
CN       101076285 A     11/2007
(Continued)

*Primary Examiner* — Patrick Fernandes
*Assistant Examiner* — Severo Antonio P Lopez
(74) *Attorney, Agent, or Firm* — Smartpat PLC

(57) ABSTRACT

A device for making available sample carriers includes a tube with a receiving chamber for a plurality of sample carriers. The receiving chamber is delimited, at its front end, by a holding means for individualized release of the sample carriers and, at its rear end, by a plunger for exerting a force on the sample carriers. The holding means is elastic. To prevent a plurality of sample carriers being released at the same time from the tube, a plurality of fins are mounted on the plunger. The fins are mutually offset in the circumferential direction of the plunger. The offset arrangement of the fins has the effect that, under the action of the force, the plunger is pressed into the interior of the tube by in each case only a predefined ejection stroke. The ejection stroke is adapted to the length or the diameter of one of the sample carriers.

11 Claims, 3 Drawing Sheets

(52) U.S. Cl.
CPC ......... *B01L 3/5023* (2013.01); *B01L 2200/04* (2013.01); *B01L 2300/087* (2013.01); *B01L 2300/0832* (2013.01)

(56) References Cited

U.S. PATENT DOCUMENTS

| | | |
|---|---|---|
| 6,390,990 B1 | 5/2002 | Marshall et al. |
| 6,523,717 B1 | 2/2003 | Willemsen |
| 8,586,382 B2 | 11/2013 | Gijlers et al. |
| 2002/0061763 A1 | 5/2002 | Weissman |
| 2008/0015470 A1 | 1/2008 | Sarstedt |
| 2008/0058676 A1 | 3/2008 | Yong |
| 2008/0281227 A1 | 11/2008 | Sarstedt |
| 2009/0131966 A1 | 5/2009 | Kheiri et al. |
| 2009/0314795 A1 | 12/2009 | Rapko et al. |
| 2012/0000299 A1 | 1/2012 | Buechner |
| 2013/0115693 A1 | 5/2013 | Holländer et al. |
| 2013/0292398 A1 | 11/2013 | Cote et al. |
| 2015/0182156 A1 | 7/2015 | Engbersen et al. |
| 2016/0279634 A1 | 9/2016 | Stemme et al. |
| 2017/0071520 A1 | 3/2017 | Rudge et al. |
| 2017/0318802 A1 | 11/2017 | Hopper |

FOREIGN PATENT DOCUMENTS

| | | |
|---|---|---|
| CN | 102131717 A | 7/2011 |
| CN | 102316989 A | 1/2012 |
| CN | 202173399 U | 3/2012 |
| CN | 103168222 A | 6/2013 |
| CN | 104582571 A | 4/2015 |
| DE | 102013201505 A1 | 7/2014 |
| JP | 2004515108 A | 5/2004 |
| JP | 2005017280 A | 1/2005 |
| JP | 2010502991 A | 1/2010 |
| SU | 398271 A1 | 9/1973 |
| WO | 2007005493 A2 | 1/2007 |
| WO | 2013067520 A1 | 5/2013 |
| WO | 2015044454 A2 | 4/2015 |
| WO | 2016074046 A1 | 5/2016 |

\* cited by examiner

DEVICE FOR MAKING AVAILABLE ABSORBENT SAMPLE CARRIERS HAVING A QUANTITY OF DRIED LIQUID, IN PARTICULAR BLOOD

CROSS-REFERENCE TO RELATED APPLICATION

This application is a National Stage application of International application PCT/EP2017/066177 filed Jun. 29, 2017 and claiming priority of German application DE 10 2016 211 911.7 filed Jun. 30, 2016.

FIELD OF THE INVENTION

The invention relates to a device for providing a dried liquid quantity, particularly blood, comprising absorbent sample carriers for analytic evaluations, wherein a supplied indeterminate liquid quantity is applied by capillary action to absorbent sample carriers and the sample carriers after drying of the quantity of liquid are delivered to a processing unit, for example a test plate.

BACKGROUND OF THE INVENTION

So-called dried-blood-spot (DBS) analysis has been known for a long time for different clinical investigations of blood samples, but also in other fields of use such as in pharmaceutical research, clinical chemistry, therapeutic medicine monitoring or forensic toxicology and doping analysis, primarily in connection with evidentially significant LC-MS/MS (liquid chromatography tandem mass spectroscopy) systems. Small drops of blood removed from the fingertip or heel of a patient are sufficient for DBS analysis. The removed blood is, as known from, for example, U.S. Pat. No. 8,586,382 B2, applied by hand to special absorbent test paper as sample carriers in circularly marked regions and after drying thereof and optionally prior storage subjected to analysis, which can be incorporated in an automated process sequence in a processing unit. Since the applied dried blood is an indeterminate quantity of liquid it is necessary in every case beforehand to desorb from the sample carrier or the marked regions of the test paper a disc of a few millimetres diameter of the material, which is dried and distributed thereon, for subsequent investigation so as to be able to provide a defined quantity of blood for the analysis or diagnosis. The disc is rinsed by a suitable solvent. After preparation of the thus-obtained extract to separate the solvent the material is available for analysis.

In order to improve the evaluating or measurement results it has become known through WO 2015/044454 A2 to more precisely determine the quantity of dried blood, which is to be desorbed from a sample carrier paper, particularly by punching out, through capillary channels. For that purpose the indeterminate removed volume of liquid is introduced into a plurality of capillary channels which each receive a specific quantity of blood and which after complete filling thereof break off the flow at the input point. As a consequence, at the outlet end of each capillary channel there is only exactly the blood quantity, which is determined or calibrated by the receiving volume of the capillary channel, in a region, which is intended for punching out, with a diameter of approximately 6 millimetres on the sample carrier paper or a sample carrier collecting card. In order that the calibrated quantity of blood can be transferred to the sample carrier collecting card a soluble membrane which, after dissolution, allows throughflow is formed at the outlet end of the capillary channels.

SUMMARY OF THE INVENTION

Starting from this prior art a device is to be created by which sample carriers for analysis can be provided in a manner which is simpler and, for the user, safer by comparison with contact with the liquid, particularly blood, especially without the requirement of desorption of individual sample carriers from a sample carrier collecting card or the like. The device according to the invention represents, in particular, an alternative to this prior art.

This object is fulfilled by the subject of claim 1. This is characterised in that the holding means is of resilient construction on the one hand for retaining the sample carriers in the receiving chamber of the tubelet and on the other hand for controlled individual release of the sample carriers from the receiving chamber under the action of force by the plunger, that a plurality of fins is arranged at the plunger at a mutual spacing in longitudinal direction of the plunger at least in the region of its plunger grip, wherein adjacent ones of the fins are offset relative to one another in circumferential direction of the plunger in each instance by a predetermined circumferential angle, and that a passage opening is provided at the rear end of the tubelet and constructed to allow the fins of the plunger to pass only in at least one predetermined circumferential angular position, also termed pass angular position in the following.

The claimed device advantageously functions as a metering dispenser for, on each occasion, exactly one sample carrier. Through the action of force on the rear end of the plunger applied by, for example, the thumb of a user the plunger is not displaced into the interior of the tubelet by an arbitrary amount, but only by a predetermined discrete travel length. This travel length corresponds with approximately the spacing between two adjacent fins. This travel length also approximately corresponds with the diameter or the length of a sample carrier; accordingly, it is also termed ejection stroke in the following. The limitation of the travel length is ensured by the claimed feature combination. In concrete terms, a leading fin initially still disposed outside the tubelet can pass the passage opening at the rear end of the tubelet only when its circumferential angular position corresponds with the pass angular position of the passage opening. However, in this case the plunger can then be urged into the interior of the tubelet only by one ejection stroke until the next adjacent trailing fin, which is initially still present outside the tubelet, appears at the passage opening. This passage opening with its pass angular position for the leading fin is then initially blocked for the trailing fin due to the offset thereof in circumferential direction. The passage opening to that extent forms an abutment for the succeeding fin and thus serves as a travel limitation for the plunger. Only when the plunger is then rotated in circumferential direction so that the angular position of the trailing fin corresponds with the pass angular position of the passage opening can the plunger be urged further into the interior of the tubelet by a further travel length, i.e. by a further ejection stroke, and thus the next sample carrier ejected from the tubelet.

The action of force or the pressure on the plunger handle is transmitted in each instance in longitudinal direction of the plunger and the tubelet by way of the plunger head from the rearmost to the foremost one of the sample carriers arranged in a row or stacked in the receiving chamber of the tubelet. The foremost sample carrier then presses directly on the holding means. If the force action is large enough then the holding means due to its resilience ultimately releases only the respective foremost sample carrier so that this can escape to the outside from the tubelet.

As stated, the claimed device particularly serves the purpose of delivering sample carriers individually to a test plate. In such a delivery process the test plate typically lies on a horizontal table and the device or tubelet according to the invention is held perpendicularly thereto.

In the present description all expressions are described by way of example with reference to this arrangement. In concrete terms, the expression "front end" accordingly means the end of the tubelet facing the test plate. It is the end where the holding means is arranged and from which the respective foremost sample carrier is in a given case released or ejected. Correspondingly, the equivalent expressions "lowermost sample carrier" or "foremost sample carrier" mean the sample carrier which is directly adjacent the holding means and next to be ejected.

Conversely, the expression "rear end" of the tubelet means the end of the tubelet remote from the test plate and the holding means or that end, which is opposite the ejecting end, where the plunger is mounted. The expression "rearmost sample carrier" to that extent analogously means the sample carrier at the end, which is remote from the holding means, of the stack of sample carriers. The expression "rearmost sample carrier" is equivalent to the expression "uppermost sample carrier".

The sample carriers by their respective predetermined receiving capacity for the liquid are themselves the reference variable for determination of the respective exact sub-quantities from the indeterminate delivered liquid quantity. It can thereby be avoided that the system has to be triggered even before drying of the determined liquid or blood quantity. The system closed by a closure therefore prevents, with greatest reliability, liquid blood from being able to penetrate to the outside. Rather, this is passed on selectively to the individual sample carriers only internally by the capillary action of the absorbent porous sample carriers, in which case each sample carrier respectively receives only a predetermined (sub-) volume of the total liquid quantity. Only when the sub-quantity has dried is the system opened and are the sample carriers sequentially ejected as described above. A punching-out process as required in the prior art is in that case completely eliminated, because the sample carriers already lie in singled form in the system which is closed when the cap is plugged on or screwed on.

Sample bodies consisting of compacted plastics material spheres, the natural surface property of which has a polarity having a capillary-promoting effect, are suitable for receiving a defined sub-quantity of the liquid. The plastics material spheres can optionally be placed in an absorbent state by surface treatment. The receiving volume of the sample carriers can in that case be determined by the intermediate spaces of the individual spheres so that variations through selection of the geometric dimensions are possible. After the successive filling of the absorbent sample bodies with the liquid sub-quantity (receiving capacity) respectively determined by them a further capillary draw is no longer present. An excess of the delivered liquid remains in the closed system, for which purpose the uppermost, i.e. the first introduced sample body of the stack layer can serve as buffer or reservoir, because the user immediately recognises with the tubelet, which consists of a transparent, i.e. clear, material, for example glass or plastic, attainment of the degree of saturation and, in particular, as soon as the blood enters the uppermost sample carrier. The feed of the indeterminate blood quantity can thereupon be interrupted without delay.

The blood can be provided, for example, from a pipette or after removal from the fingertip of a patient or, for example, also the ear lobe of an animal by means of a cannula. The tubelet is then opened by removal of the cap only for the purpose taking out the sample bodies after drying of the liquid.

Further features and details of the invention are the subject of the dependent claims.

DETAILED DESCRIPTION

Figure 1:
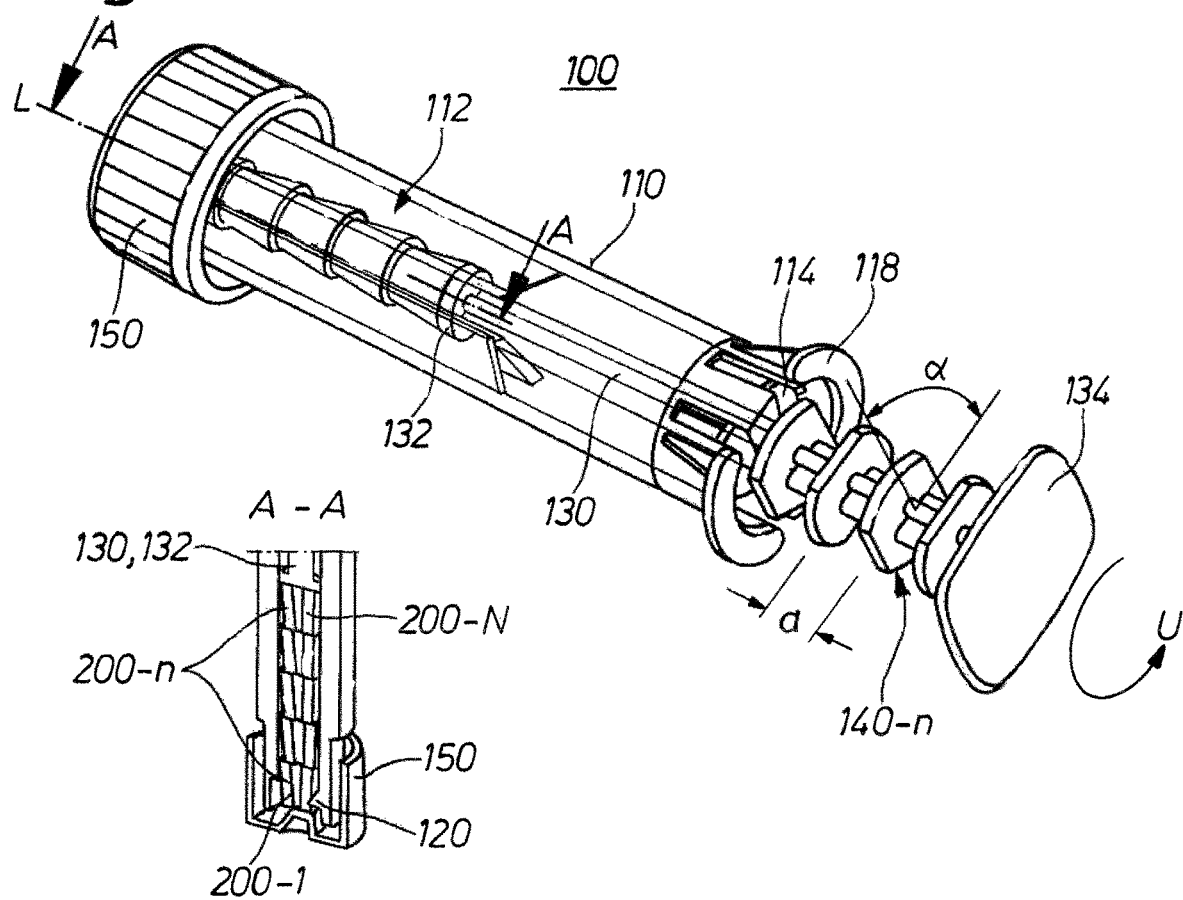
FIG. 1 shows a sample carrier tubelet in a perspective overall view in the delivery state.

The invention is described in detail in the following with reference to the mentioned figures in the form of embodiments. The same technical elements are denoted by the same reference numerals in all figures.

FIG. 1 shows a perspective overall view of the device 100 according to the invention for providing sample carriers 200-$n$, wherein $1<1<n<N$, wherein n, N are from the group of natural numbers. Each of the sample carriers 200-$n$ is constructed to accept a predetermined quantity of a liquid, for example blood.

The device 100 according to the invention comprises a tubelet 110 with a receiving chamber 112 for reception of a plurality of sample carriers 200-$n$. The receiving chamber 112 is so formed in the interior of the tubelet 110 that the individual sample carriers 200-$n$ can be arranged stacked therein in longitudinal direction L of the tubelet 110. At its front end the tubelet 110 is closed by a closure 150, for example in the form of a cap or a plug. A plunger 130 is mounted at its rear end, which is opposite the front end, to be displaceable in longitudinal direction of the tubelet. This plunger 130 enters by one end thereof in the form of a plunger head 132 into the tubelet 110 for delimitation of the receiving chamber 112 for the sample carriers. The plunger projects by its other, opposite end in the form of a plunger grip 134 out of the tubelet 110.

A plurality of fins 140-$n$ is arranged at the plunger at least in the region of the plunger grip 134 thereof. The fins are arranged at a mutual spacing in longitudinal direction L of the plunger by a predetermined spacing a. Moreover, in each instance two adjacent fins are offset relative to one another in circumferential direction U of the plunger 130 by a predetermined circumferential angle $\alpha$, wherein, for example, $\alpha=90°$.

The rear end of the tubelet 110 opposite the front end has a passage opening 114 formed to allow the fins 140-$n$ of the plunger 130 to pass only in a predetermined circumferential angular position.

The fins 140-*n* respectively extend radially from the plunger 130 or longitudinal axis L thereof.

A part longitudinal section A-A associated with FIG. 1 shows the arrangement of the sample carriers 200-*n* in the interior of the receiving chamber 112 in more detail. In concrete terms, it can be seen that the sample carriers, which by way of example are here shown as five, are arranged stacked one above the other in the interior of the receiving chamber 112. The receiving chamber 112 or the stack of sample carriers 200-*n* is bounded upwardly or towards the rear end of the tubelet by the plunger head 132 of the plunger 130. However, this boundary is not fixed, but variable in dependence on the number of sample carriers stacked one on the other.

The rear end of the tubelet 110, where the said passage opening is arranged, can be formed thereat as a radially outwardly projecting shoulder in order to increase user convenience. In concrete terms the shoulder 118 can serve as counter-holder for an index finger when the tubelet is engaged around by hand and a pressure or a force F is exerted on the plunger grip 134 by the thumb of the same hand.

The passage opening is formed as, for example, a slot which is adapted to the profile of the fin and which in each instance allows a fin to pass only in a predetermined circumferential angular position. The passage opening can also be formed to allow the fins to pass in different circumferential angular positions; however, it is then advantageous if these pass angular positions at the passage opening are not identical with the circumferential angle α between two adjacent fins 140-*n*, since the passage opening 114 otherwise cannot serve as an abutment for a trailing fin and in the case of action of force two or even more sample carriers would be ejected at the same time, which is not desired.

Figure 2:
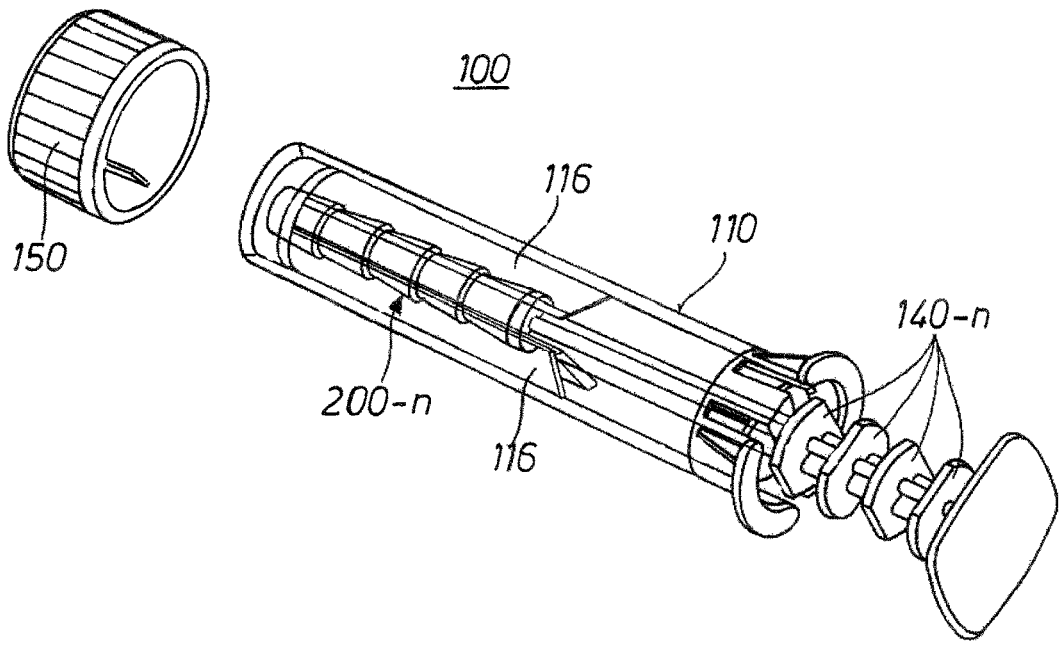
FIG. 2 shows a perspective overall view, as previously in FIG. 1, but by contrast with a cap removed for filling of an indeterminate delivered quantity of blood, so that the sample carriers are accessible.

FIG. 2 shows the device 100 as previously in FIG. 1, but now with removed cap 150. The removal of the cap is undertaken particularly for filling of the receiving chamber with the sample carriers and for filling the sample carriers with a liquid, for example blood.

Figure 3:
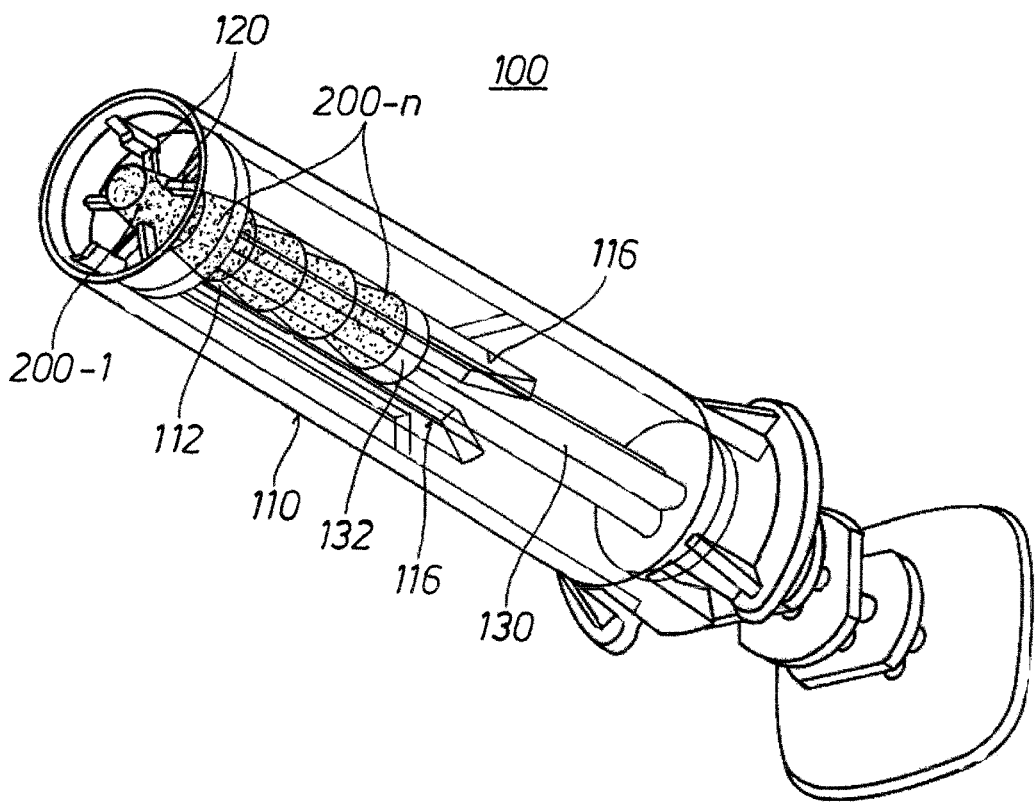
FIG. 3 shows a perspective overall view, which is different by comparison with FIG. 2 and which affords a view into the open front end of the tubelet.

FIG. 3 in turn shows another perspective view of the device 100 according to the invention, wherein this view advantageously affords a view into the front open end of the tubelet 110. The tubelet 110 is filled with sample carriers 200-*n*; the receiving chamber 112 for the sample carriers is bounded towards its rear end by the plunger head 132 and at its front end by resilient holding means 120. The holding means 120 can be constructed, for example, in the form of a resilient apertured disc or in the form of at least one resilient or resiliently mounted web, which extends in radial direction in the interior of the tubelet 110. By way of example, four holding means of that kind can be seen in FIG. 3 in distribution over the circumference. The at least one holding means serves for restraining or securing the respective foremost sample carrier 200-1.

In addition, the tubelet 110 according to FIG. 3 shows, at least in the region of its receiving chamber 112, longitudinal ribs 116 which extend in longitudinal direction of the tubelet and project radially in the interior of the tubelet 110 for radial bounding of the receiving chamber 110. By virtue of, in particular, the longitudinal ribs distributed in circumferential direction the receiving chamber 112 is so delimited in radial direction that the stack position of the sample carriers 200-*n* extends along the longitudinal axis L of the tubelet 110 and preferably concentrically in the interior of the tubelet and is supported thereat by the longitudinal ribs 116. For reasons of injection moulding, the longitudinal ribs are preferably formed integrally with the tubelet 110 and as hollow bodies protruding from the wall of the tubelet into the interior of the tubelet.

In FIGS. 3 to 6 the sample carriers are filled with the liquid, illustrated by the dotting of the sample carriers.

The device 100 according to the invention is used as follows:

In a first step the cap 150 is removed at the front end of the initially still empty tubelet 110. In a second step the receiving chamber 112 is then sequentially filled by way of the front end with individual ones of the sample carriers 200-1. At the rear end of the receiving chamber 112, the introduced sample carriers 200-*n*—supported by the head 132 of the plunger and supported in radial direction by the longitudinal ribs 116—then automatically order themselves in a stack layer. At the front end of the receiving chamber the first or foremost sample carrier 200-1 is held back in the receiving chamber by the at least one provided resilient holding means 120 even when the device 100 stands vertically and the front end is downward.

In a third step the liquid, for example blood, is then introduced through the front open end of the tubelet initially onto the foremost sample carrier 200-1. At the outset, only the first sample carrier 200-1 is then saturated by the liquid. After saturation thereof and application of even more liquid the liquid migrates from sample carrier to sample carrier due to capillary action until finally even the rearmost sample carrier 200-N is saturated or filled with the liquid. Insofar as the last (uppermost in the stack) sample carrier was used as a reservoir/buffer for an excess (indeterminate) amount of blood this sample carrier can remain in the tubelet and be discarded together with the tubelet.

Figure 4:
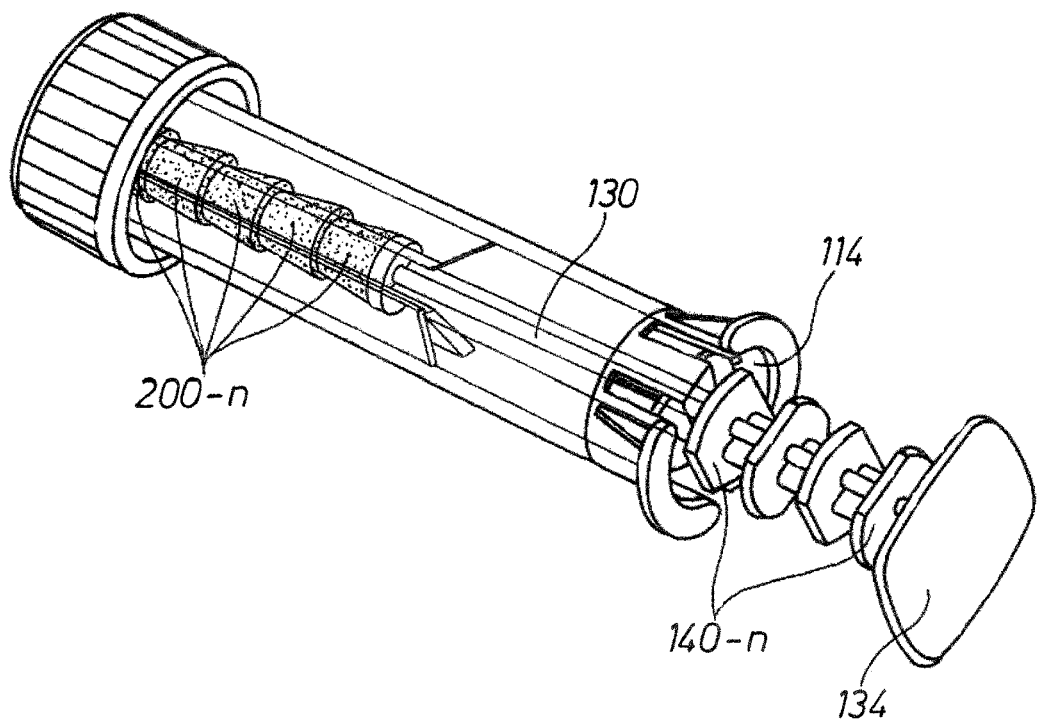
FIG. 4 shows the tubelet of FIG. 3 with closure cap fitted on for drying of the sample carriers and for transport.

In a fourth step, typically the front end of the tubelet 110 is then closed by the closure 150; see FIG. 4. The liquid in the sample carriers 210 can then dry and the tubelet with the sample carriers can be transported.

For filling of the tubelet with the sample carriers the plunger 130 is at least partly, but preferably to the greatest extent, pulled out of the tubelet. The further the plunger is pulled out, the greater is the receiving chamber 112 available for filling with the sample carriers.

Each of the sample carriers 200-*n* is constructed to be able to accept a respective precisely predetermined quantity of the liquid. The filling of the device 100 with the sample carriers and the liquid serves the purpose of being able to later separate in each instance exactly one sample carrier with the liquid quantity then contained therein, particularly to be able to apply to receiving chambers of a test plate 300.

Figure 5:
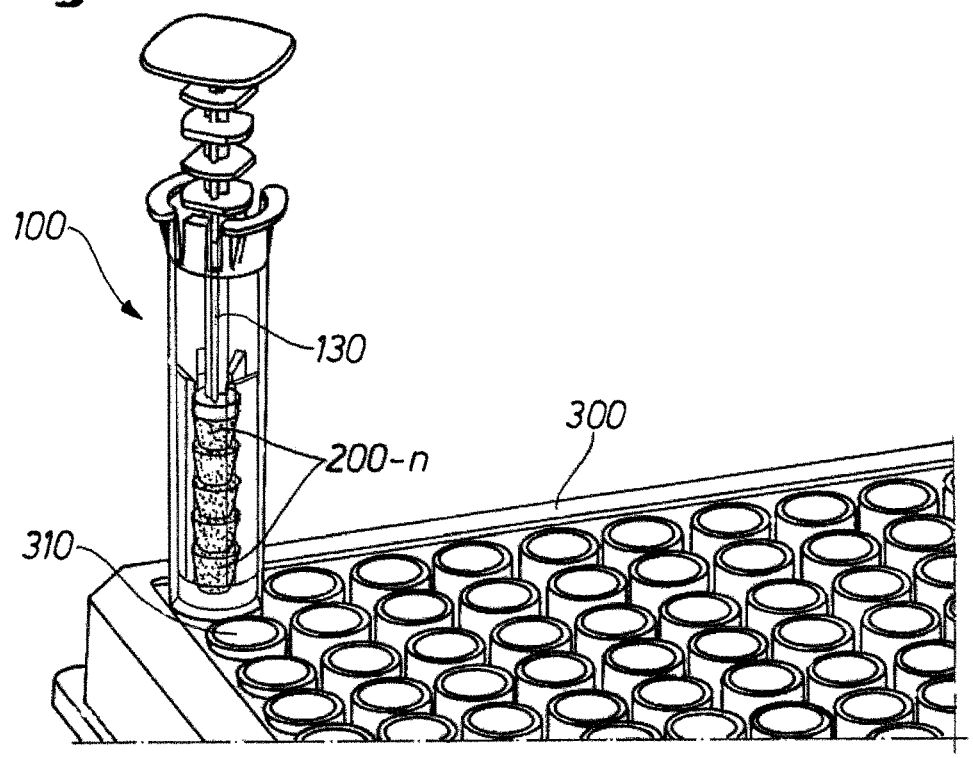
FIG. 5 shows the tubelet of FIG. 3 in a starting position placed on a test plate for ejection of the lowermost sample carrier.

For this purpose, the device according to the invention with the contained and filled sample carriers 200-*n* is, after removal of the cap 150, placed by its front open end on a respective receiving chamber 310 to be filled, as is shown in FIG. 5.

Figure 6:
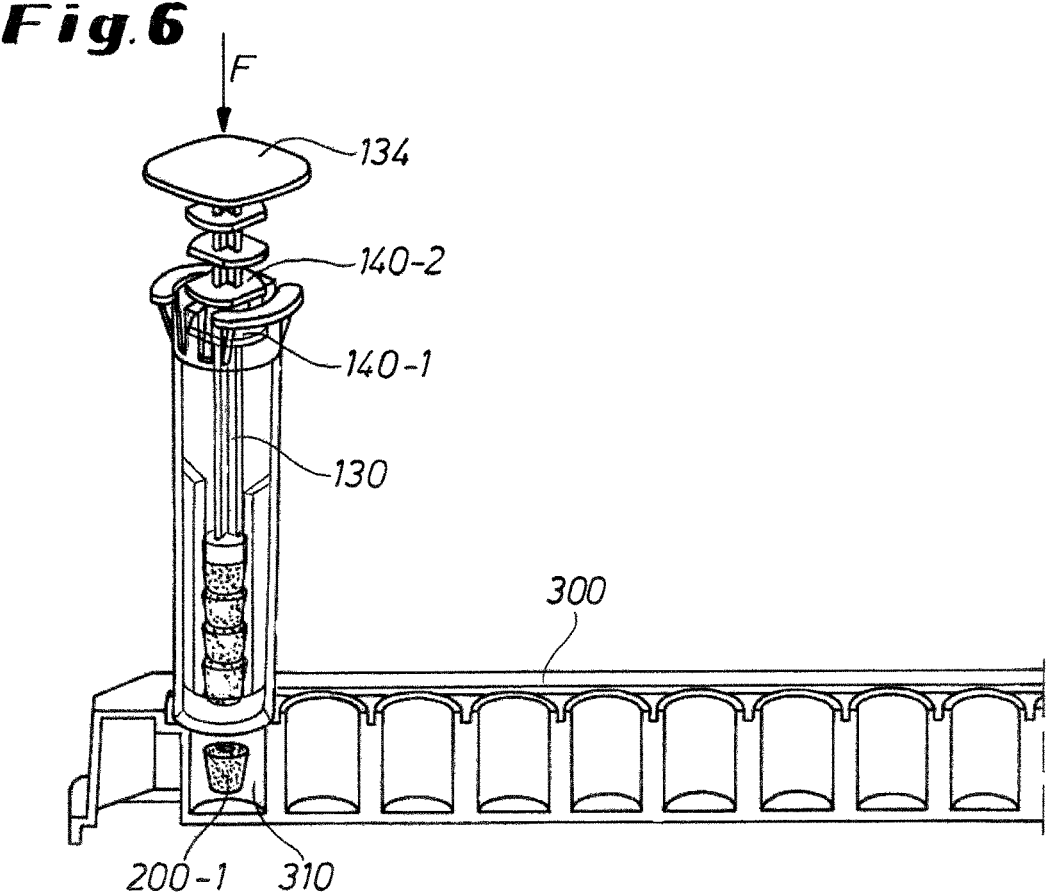
FIG. 6 shows the tubelet placed on the test plate according to FIG. 5 with the ejected foremost sample carrier.

FIG. 6 shows the delivery of the first or foremost sample carrier 200-1 into the receiving chamber 310 of the test plate 300. For this purpose, a force F is exerted from above on the plunger grip 134 typically by the hand or thumb of a user. In that case it is important for the angular position of the leading fin, which is present in front of the passage opening 114, to correspond with the circumferential angular position of the passage opening 114. Only then does the stated force F cause the leading fin 140-1 to pass the passage opening 114 and the force F to be transmitted by way of the plunger 130 and the plunger head 132 initially to the lowermost sample carrier 200-N. Due to the stacked arrangement of the sample carriers radially supported by the longitudinal ribs 116 the force then transfers from the rearmost sample carrier 200-N to the foremost sample carrier 200-1 and to the holding means 120. If the force F is large enough, then a restraining resistance of the holding means 120 is overcome and the foremost sample carrier 200-1 is then urged out of the receiving chamber 112 of the tubelet into the opening 310 of the test plate 300.

An immediately succeeding forcing of the second sample carrier 200-2 out of the receiving chamber is prevented by the fact that the travel length by which the plunger 130 is urged by the action of force into the tubelet is limited to the ejection stroke, i.e. the spacing between two adjacent fins at the plunger. In the device according to the invention this limitation is constructionally realised by the offset of two adjacent fins in circumferential direction. The leading fin 140-1 can, as stated, pass the passage opening 114 because its angular position corresponds with the pass angular position of the passage opening. However, the succeeding or trailing fin 140-2, without the plunger having been rotated in circumferential direction, initially has a different individual angular position not corresponding with the pass angular position of the passage opening 114. Because this angular position initially does not correspond with the pass angular position of the passage opening 114 the trailing fin 140-2 after the passage of the leading fin initially hits against the passage opening under the action of the force. To that extent the travel length by which the plunger is moved in the case of the action of force or the ejection stroke is limited to the spacing between the leading and the trailing fins. This ejection stroke typically corresponds with the diameter or the length or the height of one of the sample carriers 200-n. If the second sample carrier is then subsequently to be ejected into another receiving chamber 310 of the test plate 300 then the plunger 130 has to be rotated beforehand so that the previously trailing, now leading, fin corresponds in its angular position with the pass angular position of the passage opening.

REFERENCE NUMERAL LIST 100 device
110 tubelet
112 receiving chamber of the tubelet
114 passage opening
116 longitudinal ribs
118 shoulder
120 holding means
130 plunger
132 plunger head
134 plunger grip
140-1 leading fin
140-2 trailing fin
140-n fin
150 closure
200-n sample carrier
300 test plate
310 receiving chamber of the test plate
a spacing
L longitudinal direction
α circumferential angle
U circumferential direction
F force

The invention claimed is:

1. A device (100) for providing sample carriers (200-n), which are each constructed to receive a predetermined quantity of a liquid, comprising:

a tubelet (110) with a receiving chamber (112) in an interior thereof for reception of a plurality of sample carriers stacked in a longitudinal direction (L) of the tubelet (110);
a holding means (120), which is arranged at a front end of the tubelet, for bounding the receiving chamber (112) at one end; and
a plunger (130), which is mounted at a rear end of the tubelet to be displaceable in the longitudinal direction (L) of the tubelet, the plunger having a plunger head (132) which enters into the tubelet (110) for bounding the receiving chamber oppositely to the holding means
(120) at one end of the plunger (130) and
a plunger grip (134) which projects out of the tubelet at an opposite end of the plunger (130),
wherein the holding means (120) is of resilient construction for retaining the sample carriers (200-n) in the receiving chamber (112) and for controlled individual release of the sample carriers (200-n) from the receiving chamber (112) under action of a force by the plunger (130);
wherein a plurality of fins (140-n) is arranged at the plunger (130) at least in a region of the plunger grip thereof to be spaced from one another by a spacing in longitudinal direction (L) of the plunger, wherein adjacent fins are arranged to be offset relative to one another in a circumferential direction (U) of the plunger (130) each time by a predetermined circumferential angle (α), and
wherein a passage opening (114) formed to allow the fins (140-n) of the plunger (130) to pass only in at least one predetermined circumferential angular position is provided at the rear end of the tubelet (110).

2. The device (100) according to claim 1, wherein the fins (140-n) each extend radially from the plunger (130).

3. The device (100) according to claim 1, wherein the circumferential angle (α) about which each two adjacent fins are arranged on the plunger to be offset relative to one another is α=90°.

4. The device (100) according to claim 1, wherein the spacing (a) between each two adjacent fins corresponds at least approximately with a diameter or a length of one of the sample carriers (200-n).

5. The device (100) according to claim 1, wherein the tubelet (110) has at least in the region of the receiving chamber (112) longitudinal ribs (116) which are distributed over its circumference and which extend in the longitudinal direction (L) of the tubelet and project radially into the interior of the tubelet for radial bounding of the receiving chamber.

6. The device (100) according to claim 5, wherein the longitudinal ribs (116) are formed integrally with the tubelet (110) and as hollow bodies protruding from a wall of the tubelet into the interior of the tubelet.

7. The device (100) according to claim 1, further comprising a closure (150) in form of a cap or plug for closing the front end of the tubelet (110).

8. The device (100) according to claim 1, wherein the tubelet (110) is made from a transparent material.

9. The device (100) according to claim 1, wherein the holding means (120) is a resilient apertured disc or at least one resilient web or resiliently mounted web, the disc or web extending in radial direction in the interior of the tubelet (110).

10. The device (100) according to claim 1, wherein the liquid is blood.

11. The device (100) according to claim 8, wherein the transparent material is glass or plastic.

\* \* \* \* \*